US012599308B2

(12) United States Patent
Wassertheurer

(10) Patent No.: US 12,599,308 B2
(45) Date of Patent: Apr. 14, 2026

(54) SENSOR DEVICE, SYSTEM, AND METHOD FOR PERFORMING AN ABSOLUTE BLOOD PRESSURE MEASUREMENT

(71) Applicant: AIT AUSTRIAN INSTITUTE OF TECHNOLOGY GMBH, Vienna (AT)

(72) Inventor: Siegfried Wassertheurer, Bad Gleichenberg (AT)

(73) Assignee: AIT AUSTRIAN INSTITUTE OF TECHNOLOGY GMBH, Vienna (AT)

( * ) Notice: Subject to any disclaimer, the term of this patent is extended or adjusted under 35 U.S.C. 154(b) by 339 days.

(21) Appl. No.: 18/256,162

(22) PCT Filed: Dec. 9, 2021

(86) PCT No.: PCT/EP2021/084943
§ 371 (c)(1),
(2) Date: Jun. 6, 2023

(87) PCT Pub. No.: WO2022/122893
PCT Pub. Date: Jun. 16, 2022

(65) Prior Publication Data
US 2024/0041336 A1 Feb. 8, 2024

(30) Foreign Application Priority Data
Dec. 9, 2020 (EP) ..................................... 20212903

(51) Int. Cl.
*A61B 5/021* (2006.01)
*A61B 5/00* (2006.01)
(Continued)

(52) U.S. Cl.
CPC ........ *A61B 5/02125* (2013.01); *A61B 5/0205* (2013.01); *A61B 5/053* (2013.01);
(Continued)

(58) Field of Classification Search
CPC ... A61B 5/02125; A61B 5/0205; A61B 5/053; A61B 5/33; A61B 5/6843; A61B 5/024;
(Continued)

(56) References Cited

U.S. PATENT DOCUMENTS

2016/0213331 A1* 7/2016 Gil ......................... A61B 5/389
2017/0251935 A1 9/2017 Yuen
(Continued)

FOREIGN PATENT DOCUMENTS

DE 102012007081 B4 10/2013
DE 102019104568 A1 10/2019
(Continued)

OTHER PUBLICATIONS

International Search Report and Written Opinion in corresponding International Application No. PCT/EP2021/084943 dated Mar. 18, 2022.
(Continued)

*Primary Examiner* — Brian T Gedeon
(74) *Attorney, Agent, or Firm* — Westman, Champlin & Koehler, P.A.

(57) ABSTRACT

A sensor device or system for performing a blood pressure measurement comprises a finger abutment surface, a first sensor operative to sense blood volume pulses in a finger pressed on the finger abutment surface, a second sensor operative to sense a force or pressure with which the finger is pressed on the finger abutment surface, and processing circuitry operative to process amplitudes of the sensed blood volume pulses and the sensed force or pressure with which the finger is pressed on the finger abutment surface to determine an absolute blood pressure.

17 Claims, 8 Drawing Sheets

(51) Int. Cl.
| | |
|---|---|
| *A61B 5/0205* | (2006.01) |
| *A61B 5/022* | (2006.01) |
| *A61B 5/024* | (2006.01) |
| *A61B 5/0245* | (2006.01) |
| *A61B 5/0295* | (2006.01) |
| *A61B 5/053* | (2021.01) |
| *A61B 5/33* | (2021.01) |

(52) U.S. Cl.
CPC .............. *A61B 5/33* (2021.01); *A61B 5/6843* (2013.01); *A61B 5/024* (2013.01); *A61B 2560/0223* (2013.01); *A61B 2562/0247* (2013.01)

(58) Field of Classification Search
CPC .... A61B 2560/0223; A61B 2562/0247; A61B 5/02225; A61B 5/02141; A61B 2560/0238; A61B 2560/0406; A61B 2560/0468; A61B 5/0245; A61B 5/0295
See application file for complete search history.

(56) References Cited

U.S. PATENT DOCUMENTS

| | | | |
|---|---|---|---|
| 2019/0008399 A1* | 1/2019 | Mukkamala | ......... A61B 5/0261 |
| 2020/0113442 A1 | 4/2020 | Yuan | |

FOREIGN PATENT DOCUMENTS

| | | | |
|---|---|---|---|
| WO | 2009112000 A1 | 9/2009 |
| WO | 2019243629 A1 | 12/2019 |

OTHER PUBLICATIONS

European Search Report in corresponding European application No. 20212903.7 dated Jun. 6, 2021.

\* cited by examiner

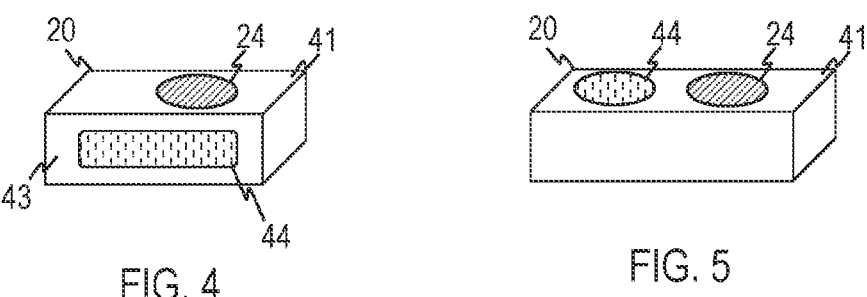
FIG. 4
FIG. 5
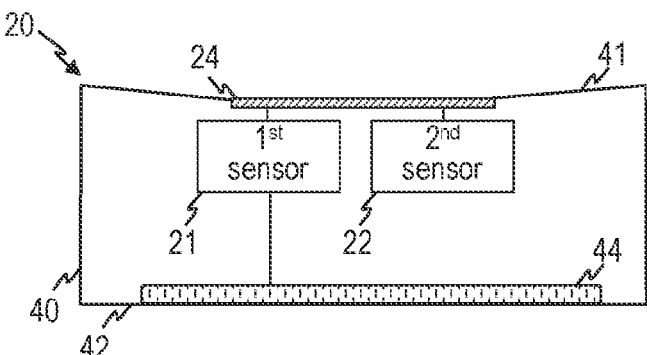
FIG. 6
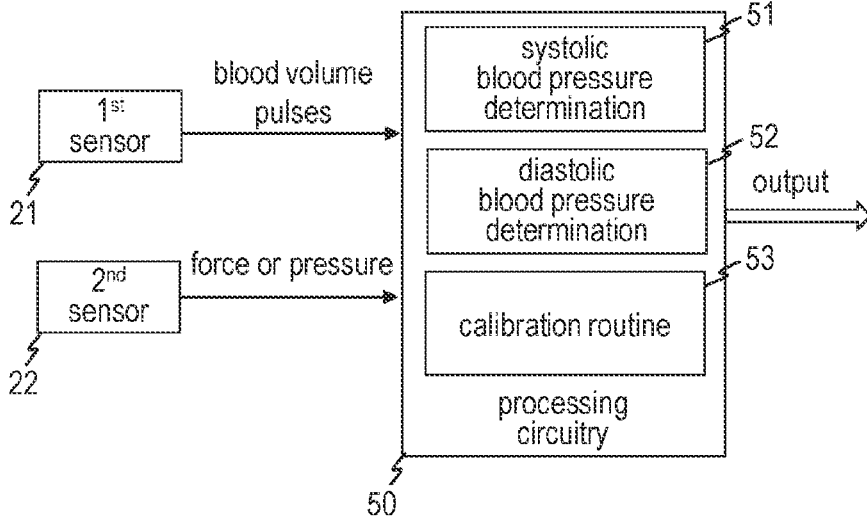
FIG. 7

90

91 Estimating absolute value of blood pressure using PTT-based blood pressure monitoring 92 Generating user instructions for guiding user to adjust force exerted on finger abutment surface 93 Determining absolute value of blood pressure based on first sensor output and second sensor output 94 Calibration of PTT-based blood pressure monitoring

10

SENSOR DEVICE, SYSTEM, AND METHOD FOR PERFORMING AN ABSOLUTE BLOOD PRESSURE MEASUREMENT

CROSS-REFERENCE TO RELATED APPLICATIONS

The present application is a § 371 national phase entry of International patent application Serial No. PCT/EP2021/084943, filed Dec. 9, 2021, and published in English, and claims priority from EP application no. 20212903.7 filed on Dec. 9, 2020.

TECHNICAL FIELD

The invention relates to devices, systems, and methods for performing blood pressure measurements.

BACKGROUND

Hypertension is a medical condition that causes widespread concern in many countries worldwide. The fraction of the population suffering from hypertension continues to increase in many countries. Blood pressure measurements are important for people suffering from hypertension. Even when a person is not suffering from hypertension, blood pressure measurements are of significant relevance in order to monitor the effects of behavioral patterns (such as physical exercise or lack thereof) on the person's blood pressure.

Conventional blood pressure measurement techniques rely on cuffs that are releasably mounted onto the upper arm, inflated, and subsequently deflated. The use of such cuffs adds to the inconvenience associated with a blood pressure measurement. Incorrect cuff positioning is a reason for incorrect blood pressure measurements, in particular when carried out by non-trained persons.

In order to mitigate the inconvenience associated with blood pressure measurements using inflatable cuffs, techniques have been proposed that process sensor signals associated with volume pulses and/or that try to infer changes in blood pressure from a change in heart rate. Techniques that try to infer changes in blood pressure from heart rate variability are disclosed in, e.g., WO 2009/112000 A1, which discloses an apparatus for determining cardiovascular variability that uses non-invasively recorded blood pressure signals for analysis. DE 10 2012 007 081 B4 and DE 10 2019 104 568 A1 disclose techniques in which pulsating signals are evaluated.

US 2017/0251935 A1, WO 2019/243629 A1, and US 2020/0113442 A1 disclose measuring devices comprising various sensors.

Conventional approaches for cuffless blood pressure measurements are prone to being inaccurate and/or require electromechanical actuators which may add to the complexity of the measurement devices, increase the risk of component failure, and reduce the speed and convenience of the blood pressure measurement. The use of electromechanical actuators also increases power consumption per measurement. As a consequence, devices that use electromechanical actuators are prone to experiencing high battery power consumption or require a connection to a power grid, which limits the field of use of such devices and/or which requires frequent battery replacement or recharging. Some conventional techniques that do not require electromechanical actuators allow relative changes of blood pressure to be determined, but do not allow absolute values of the blood pressure to be reliably measured.

SUMMARY

There is a need for improved devices, systems, and methods for performing blood pressure measurements. There is in particular a need for devices, systems, and methods for performing blood pressure measurements that can provide short measurement time, be used in a convenient manner, mitigate the risk of component failure associated with a pump or another electromechanical actuator, and/or operate at a lower power consumption than, e.g., systems having a cuff inflated by a pump.

According to the invention, measurements of blood volume pulses in a finger are processed in combination with measurements of a force and/or pressure with which the finger is pressed against a finger abutment surface. Absolute values of systolic, diastolic, and/or mean blood pressure can be determined without using a pump or another electromechanical actuator.

As used herein, the term "absolute value" refers to the pressure (in any suitable values), in contrast to a relative change in pressure that does not provide reliably information on the absolute value.

In devices, systems, and methods according to the invention, the pressure or force at which a user presses a finger on the finger abutment surface is utilized to temporarily cause and then suppress blood pulsation in the finger, and to determine the pressure at which the blood pulsation in the finger is temporarily suppressed as the force exerted onto the finger abutment surface increases and/or the pressure at which the blood pulsation in the finger is recovered as the force exerted onto the finger abutment surface decreases.

The techniques according to the invention do not require a pump or other electromechanical actuator for determining absolute values of systolic, diastolic, and/or mean blood pressure. Thus, the devices, systems, and methods according to the invention mitigate the problems associated with electromechanical actuators, such as high power consumption, slow measurement times, high risk of electromechanical component failure, and/or user inconvenience.

The blood volume pulses may be sensed using a bioimpedance sensor. The finger abutment surface may be conductive and may operate as an electrode of the bioimpedance sensor. This allows blood volume pulses and their amplitudes to be determined using robust components that measure impedance. The force and/or pressure may be measured using a resistive, capacitive, or inductive sensor.

The devices, systems, and methods according to the invention may conveniently combine (i) a blood pressure measurement in which an absolute value of the blood pressure is determined by processing measurements of blood volume pulses in a finger and measurements of a force and/or pressure with which the finger is pressed against the finger abutment surface and (ii) measurements that determine relative changes in blood pressure, such as pulse transit time (PTT)-based techniques. The absolute value of the blood pressure determined by processing the measurements of blood volume pulses in a finger and measurements of a force and/or pressure with which the finger is pressed against the finger abutment surface can be used in combination with PTT-based techniques, e.g., for calibrating the PTT-based technique.

A sensor device or system according to an aspect of the invention is configured for performing a blood pressure measurement and comprises a finger abutment surface, a first sensor operative to sense blood volume pulses in a finger pressed on the finger abutment surface, a second sensor operative to sense a force or pressure with which the finger may be pressed on the finger abutment surface, and processing circuitry. The processing circuitry is operative to process amplitudes of the sensed blood volume pulses and the sensed force or pressure with which the finger is pressed on the finger abutment surface to determine an absolute blood pressure.

The first sensor may be operative to sense any measurement quantity that is directly or indirectly indicative of blood volume pulses. For illustration, optical measurements may be directly indicative of blood volume pulses, while impedance measurement may be indirectly indicative of blood volume pulses.

The first sensor may comprise a bioimpedance sensor.

The finger abutment surface may be conductive and may operate as one electrode of the bioimpedance sensor.

The bioimpedance sensor may comprise a bioimpedance sensor surface that is conductive.

The bioimpedance sensor surface may be arranged transversely to the finger abutment surface. A housing of the sensor device may comprise a first surface on which the finger abutment surface is arranged and a second surface arranged at an angle relative to the first surface, with the bioimpedance sensor surface being arranged on the second surface so as to extend at an angle (i.e., not coplanar and not parallel) to the finger abutment surface.

The bioimpedance sensor surface may be offset relative to the finger abutment surface. The bioimpedance sensor surface and the finger abutment surface may be arranged on a first surface of a housing of the sensor device, with the bioimpedance sensor surface being laterally offset from the finger abutment surface along the first surface. The finger abutment surface may be arranged on a first surface of a housing of the sensor device and the bioimpedance sensor surface may be arranged on a second surface of the housing which extends parallel to and offset from the first surface.

The sensor device or system may be operative to concurrently sense the blood volume pulses and pressure or force.

The sensor device or system may be operative to sense the blood volume pulses and pressure or force in a time-resolved manner.

The first sensor may provide the sensed blood volume pulses as time-series data.

The second sensor may provide the sensed pressure or force as time-series data.

The processing circuitry may be operative to determine pulse transit times (PTTs) of the blood volume pulses and to process the PTTs to determine a change in blood pressure.

The processing circuitry may be operative to process an output of an electrocardiogram (ECG) sensor and, optionally, of the first sensor to determine the PTTs.

The processing circuitry may be operative to control a user interface based on an ECG signal sensed by the ECG sensor.

The processing circuitry may be operative to control the user interface based on at least one of the PTTs.

The system may comprise the ECG sensor.

The processing circuitry may be operative to execute a calibration routine for calibrating a PTT-based blood pressure monitoring process.

The calibration routine may use, as an input, the absolute blood pressure determined based on the amplitudes of the sensed blood volume pulses and the sensed force or pressure.

The processing circuitry may be operative to generate user instructions for adjusting the force or pressure based on measured PTTs.

The first sensor may comprise at least one of: a photoplethysmography, PPG, sensor, a piezoelectric sensor, an accelerometer, in particular a ballistographic sensor.

The processing circuitry may be operative to process the amplitudes of the sensed blood volume pulses and the sensed force or pressure to determine one or several of: a systolic blood pressure, a diastolic blood pressure, a mean blood pressure that is a mean value of the systolic and diastolic blood pressures.

The processing circuitry may be operative to determine the systolic blood pressure based on the force or pressure sensed by the second sensor in at least one pulse before the amplitude of the blood volume pulses sensed by the first sensor reaches a threshold or falls below the threshold as the force or pressure increases and/or based on the force or pressure sensed by the second sensor in at least one pulse before the amplitude of the blood volume pulses sensed by the first sensor reaches another threshold or exceeds the other threshold as the force or pressure decreases.

The processing circuitry may be operative to perform an extrapolation of the forces or pressures detected for at least two blood volume pulses before the amplitude of the blood volume pulses reaches a threshold or falls below the threshold.

The processing circuitry may be operative to determine the systolic blood pressure based on the amplitudes of the blood volume pulses and the force or pressure sensed while the force or pressure increases.

The processing circuitry may be operative to determine the diastolic blood pressure based on a change in the amplitudes of the sensed blood volume pulses as a function of the sensed force or pressure.

The processing circuitry may be operative to determine the diastolic blood pressure based on the force or pressure sensed by the second sensor in at least one pulse before the amplitude of the blood volume pulses sensed by the first sensor reaches a threshold or exceeds a threshold while the force or pressure increases or based on the force or pressure sensed by the second sensor in at least one pulse before the amplitude of the blood volume pulses sensed by the first sensor reaches another threshold or falls below the other threshold while the force or pressure decreases.

The processing circuitry may be operative to perform an extrapolation of the forces or pressures detected for at least two blood volume pulses before the amplitude of the blood volume pulses reaches the other threshold or falls below the other threshold while the force or pressure decreases.

The processing circuitry may be operative to determine the diastolic blood pressure based on the systolic blood pressure and the mean blood pressure.

The processing circuitry may be operative to determine the mean blood pressure based on amplitudes of the sensed blood pressure pulses as a function of sensed pressure or force.

The processing circuitry may be operative to determine one or several of the systolic blood pressure, the diastolic blood pressure, the mean blood pressure from the first and second sensor outputs recorded while the force or pressure increases.

The processing circuitry may be operative to determine one or several of the systolic blood pressure, the diastolic blood pressure, the mean blood pressure from the first and second sensor outputs recorded while the force or pressure decreases.

The processing circuitry may be operative to determine one or several of the systolic blood pressure, the diastolic blood pressure, the mean blood pressure from the first and second sensor outputs recorded while the force or pressure varies non-monotonously, i.e., exhibits an increase followed by a decrease or vice versa.

The sensor device or system may further comprise a user interface operative to output user instructions to cause the user to change the force or pressure.

The user interface may be operative to output instructions to increase the force or pressure with which the finger is pressed against the finger abutment surface.

The user interface may be operative to output instructions to decrease the force or pressure with which the finger is pressed against the finger abutment surface.

The user interface may be operative to output instructions to change the force or pressure with which the finger is pressed against the finger abutment surface in a non-monotonous manner.

Alternatively or additionally, the user interface may be operative to output information indicating the determined blood pressure.

The sensor device may be a cuffless sensor device or the system may be a cuffless system.

The sensor device or system may be operative to determine the absolute blood pressure without activation of a pump.

The sensor device or system may be operative to determine the absolute blood pressure without activation of an electromechanical actuator.

The sensor device or system may comprise a communication interface for communicatively coupling the first and second sensors to at least part of the processing circuitry.

The sensor device or system of may further comprise a housing comprising the finger abutment surface.

The first sensor, the second sensor, and the communication interface may be arranged in or on the housing.

The housing may comprise a depression in which the finger abutment surface may be arranged.

The sensor device or system may further comprise a bearing surface opposite the finger abutment surface and operative to provide a counter-bearing to the force or pressure with which the user presses the finger on the finger abutment surface.

The bearing surface may include a sensor surface of the first or second sensor.

The second sensor may comprise a resistive, capacitive, or inductive sensor.

A method of performing a blood pressure measurement comprises receiving a first sensor output representing sensed blood volume pulses in a finger pressed on a finger abutment surface, receiving a second sensor output representing a sensed force or pressure with which the finger is pressed on the finger abutment surface, and processing, by processing circuitry, amplitudes of the sensed blood volume pulses and the sensed force or pressure to determine an absolute blood pressure.

The first sensor output may be sensed using a bioimpedance sensor.

The method may comprise sensing the blood volume pulses using the bioimpedance sensor.

The finger abutment surface may be conductive and may operate as one electrode of the bioimpedance sensor.

The blood volume pulses and pressure or force may be sensed concurrently.

The blood volume pulses and pressure or force may be sensed in a time-resolved manner.

The first sensor output may include time-series data indicating the sensed blood volume pulses as a function of time.

The second sensor output may include time-series data indicating the sensed pressure or force as a function of time.

The method may comprise determining pulse transit times (PTTs) of the blood volume pulses and processing the PTTs to determine a change in blood pressure.

The method may comprise processing an output of an electrocardiogram (ECG) sensor and, optionally, of the first sensor to determine the PTTs.

The method may comprise controlling a user interface based on an ECG signal sensed by the ECG sensor.

The user interface may be controlled based on at least one of the PTTs.

The method may comprise executing a calibration routine for calibrating a PTT-based blood pressure monitoring process.

The calibration routine may use, as an input, the absolute blood pressure determined based on the amplitudes of the sensed blood volume pulses and the sensed force or pressure.

The method may comprise generating user instructions for adjusting the force or pressure based on measured PTTs.

The first sensor may comprise at least one of: a photoplethysmography, PPG, sensor, a piezoelectric sensor, an accelerometer, in particular a ballistographic sensor.

The method may comprise processing the amplitudes of the sensed blood volume pulses and the sensed force or pressure to determine one or several of: a systolic blood pressure, a diastolic blood pressure, a mean blood pressure that is a mean value of the systolic and diastolic blood pressures.

The method may comprise determining the systolic blood pressure based on the force or pressure sensed by the second sensor in at least one pulse before the amplitude of the blood volume pulses sensed by the first sensor reaches a threshold or falls below the threshold as the force or pressure increases and/or based on the force or pressure sensed by the second sensor in at least one pulse before the amplitude of the blood volume pulses sensed by the first sensor reaches another threshold or exceeds the other threshold as the force or pressure decreases.

The method may comprise performing an extrapolation of the forces or pressures sensed for at least two blood volume pulses before the amplitude of the blood volume pulses reaches a threshold or falls below the threshold.

The method may comprise determining the systolic blood pressure based on the amplitudes of the blood volume pulses and the force or pressure sensed while the force or pressure increases.

The method may comprise determining the diastolic blood pressure based on a change in the amplitudes of the sensed blood volume pulses as a function of the sensed force or pressure.

The method may comprise determining the diastolic blood pressure based on based on the force or pressure sensed by the second sensor in at least one pulse before the amplitude of the blood volume pulses sensed by the first sensor reaches a threshold or exceeds a threshold while the force or pressure increases or the force or pressure sensed by the second sensor in at least one pulse before the amplitude of the blood volume pulses sensed by the first sensor reaches another threshold or falls below the other threshold while the force or pressure decreases.

The method may comprise performing an extrapolation of the forces or pressures sensed for at least two blood volume pulses before the amplitude of the blood volume pulses reaches the other threshold or falls below the other threshold while the force or pressure decreases.

The method may comprise determining the diastolic blood pressure based on the systolic blood pressure and the mean blood pressure.

The method may comprise determining the mean blood pressure based on amplitudes of the sensed blood pressure pulses as a function of sensed pressure or force.

The method may comprise determining one or several of the systolic blood pressure, the diastolic blood pressure, the mean blood pressure from the first and second sensor outputs recorded while the force or pressure increases.

The method may comprise determining one or several of the systolic blood pressure, the diastolic blood pressure, the mean blood pressure from the first and second sensor outputs recorded while the force or pressure decreases.

The method may comprise determining one or several of the systolic blood pressure, the diastolic blood pressure, the mean blood pressure from the first and second sensor outputs recorded while the force or pressure varies non-monotonously, i.e., exhibits an increase followed by a decrease or vice versa.

The method may comprise controlling a user interface to output user instructions to cause the user to change the force or pressure.

The method may comprise controlling the user interface to output user instructions to increase the force or pressure with which the finger is pressed against the finger abutment surface.

The method may comprise controlling the user interface to output user instructions to decrease the force or pressure with which the finger is pressed against the finger abutment surface.

The method may comprise controlling the user interface to output user instructions to change the force or pressure with which the finger is pressed against the finger abutment surface in a non-monotonous manner.

The method may comprise controlling a user interface to output information indicating the determined blood pressure.

The method may be performed without using a cuff.

The method may be performed without activation of a pump.

The method may be performed without activation of an electromechanical actuator.

The method may comprise receiving the first sensor output and the second sensor output at a communication interface and providing the first sensor output and the second sensor output to at least part of the processing circuitry.

The second sensor may comprise a resistive, capacitive, or inductive sensor.

The method may be performed by the sensor device or system of an embodiment.

The method may be employed for performing blood pressure measurements for providing biofeedback.

The method may be employed for performing blood pressure measurements for monitoring blood pressure changes in response to user behavior (such as physical exercise or the absence thereof) in a non-medical environment.

According to another aspect of the invention, there is provided computer-executable instruction code comprising instructions which, when executed by at least one integrated circuit of a computing device, cause the computing device to perform the method according to an embodiment.

According to another aspect of the invention, there is provided a tangible storage medium with computer-executable instruction code comprising instructions which, when executed by at least one integrated circuit of a computing device, cause the computing device to perform the method according to an embodiment.

Various effects and advantages are associated with the invention. The devices, systems, and methods for performing blood pressure measurements according to the invention do not require a cuff, pump or other electromechanical actuator for determining absolute values of systolic, diastolic, and/or mean blood pressure. Thus, the devices, systems, and methods according to the invention mitigate problems such as high power consumption, slow measurement times, and/or high risk of electromechanical component failure.

The devices, systems, and methods for performing blood pressure measurements according to the invention do not require a cuff. The devices, systems, and methods according to the invention can be readily used in a manner that is considered less intrusive and less cumbersome by users.

The devices, systems, and methods for performing blood pressure measurements can be easily combined with techniques that allow relative changes in blood pressure to be determined (such as PTT-based techniques). For illustration, techniques that allow relative changes in blood pressure to be determined may be calibrated using the blood pressure determined from amplitudes of blood volume pulses and a force or pressure with which a finger is pressed against a finger abutment surface.

The present summary is provided only by way of example and not limitation. Other aspects of the present invention will be appreciated in view of the entirety of the present disclosure, including the entire text, claims, and accompanying figures.

BRIEF DESCRIPTION OF THE DRAWINGS

Embodiments of the invention will be described with reference to the drawings in which elements having identical or similar structure or function are designated with identical or similar reference signs.

FIG. 4 is a schematic view of a sensor device.

FIG. 5 is a schematic view of a sensor device.

FIG. 6 is a schematic view of a sensor device.

FIG. 7 is a functional block diagram representation of components of the sensor device and/or system.

Figure 1:
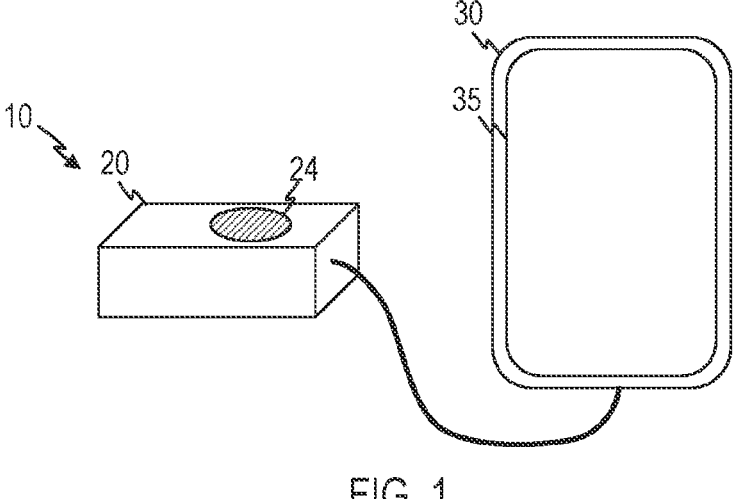
FIG. 1 is a schematic view of a system.

While the above-identified figures set forth one or more embodiments of the present invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features, steps, and/or components not specifically shown in the drawings.

DETAILED DESCRIPTION OF EMBODIMENTS

Embodiments of the invention will be described with reference to the drawings. The features of the various embodiments may be combined with each other, unless this is expressly excluded in the following description.

While embodiments will be described in association with certain sensors and/or certain processing techniques, the embodiments are not limited to the specific sensors or processing techniques.

FIG. 1 is a schematic representation of a system 10 according to an embodiment. The system 10 is operative to determine absolute value(s) (and not only changes) of one or several of a systolic blood pressure, a diastolic blood pressure, a mean blood pressure that is a mean value of the systolic and diastolic blood pressures. The system 10 comprises a sensor device 20 and a computing device 30. The computing device 30 may be a portable communication terminal, a computer, or a server communicatively coupled to the sensor device 20. The sensor device 20 may be a dedicated accessory to a computing device or may be a portable communication terminal.

The sensor device 20 comprises a finger abutment surface 24. The finger abutment surface 24 is provided in a surface of a housing. The sensor device 20 is operative to sense blood volume pulses at the finger abutment surface 24 when a finger is pressed against the finger abutment surface 24. The sensor device 20 is operative to sense a pressure or force with which the finger is pressed against the finger abutment surface 24.

The sensor device 20 and/or the computing device 30 is/are operative to process amplitudes of the blood volume pulses and the sensed pressure or force with which the finger is pressed against the finger abutment surface 24.

The system 20 may be operative to generate output indicative of the determined blood pressure and/or instructions to the user for increasing the force applied by the finger to the finger abutment surface 24 and/or instructions to the user for decreasing the force applied by the finger to the finger abutment surface 24. The output may be output via a user interface 35 of the computing device 30.

Figure 2:
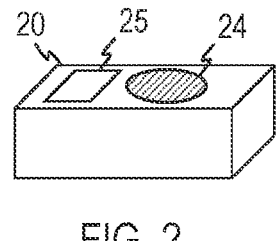
FIG. 2 is a schematic view of a sensor device.

FIG. 2 shows an embodiment in which the sensor device 20 has a user interface 25. The sensor device 20 may be operative to generate output indicative of the determined blood pressure and/or instructions to the user for increasing the force applied by the finger to the finger abutment surface 24 and/or instructions to the user for decreasing the force applied by the finger to the finger abutment surface 24, and to control the user interface 25 to output this information.

The user interface 25, 35 may comprise a graphical user interface. The user interface 25, 35 may comprise an acoustic user interface.

The sensor device 20 and/or the computing device 30 may comprise one or several integrated circuit(s) (IC(s)). The one or several integrated circuit(s) (IC(s)) may comprise one or several of a processor, controller, field programmable gate array (FPGA), an application specific integrated circuit (ASIC), or any combination of such integrated circuits. The one or several IC(s) may be operative to determine the systolic blood pressure based on the pressure or force applied by the finger to the finger abutment surface 24 at a time at which the blood volume pulses sensed at the finger abutment surface 24 have the last maximum that is greater than a first threshold, when the pressure or force applied by the finger to the finger abutment surface 24 increases. The one or several IC(s) may be operative to determine the systolic blood pressure based on the pressure or force applied by the finger to the finger abutment surface 24 by performing an extrapolation that takes into account the amplitudes of at least two blood volume pulses sensed at the finger abutment surface 24 and the pressures or forces applied to the finger abutment surface 24 at the times at which maxima of the at least two blood volume pulses are recorded while the pressure or force applied by the finger to the finger abutment surface 24 increases.

The one or several IC(s) may be operative to determine the diastolic blood pressure. The one or several IC(s) may be operative to determine the diastolic blood pressure based on the pressure or force applied by the finger to the finger abutment surface 24 at a time at which the blood volume pulses sensed at the finger abutment surface 24 have the last maximum that is greater than a second threshold (which may be equal to or different from the first threshold), when the pressure or force applied by the finger to the finger abutment surface 24 decreases. The one or several IC(s) may be operative to determine the diastolic blood pressure based on the pressure or force applied by the finger to the finger abutment surface 24 by performing an extrapolation that takes into account the amplitudes of at least two blood volume pulses sensed at the finger abutment surface 24 and the pressures or forces applied to the finger abutment surface 24 at the times at which maxima of the at least two blood volume pulses are recorded while the pressure or force applied by the finger to the finger abutment surface 24 decreases.

The one or several IC(s) may be operative to determine the mean blood pressure and one of the systolic and diastolic blood pressures based on a dependence of an amplitude of the blood volume pulses sensed at the finger abutment surface 24 on the pressure or force applied by the finger to the finger abutment surface 24. The one or several IC(s) may be operative to determine the other one of the systolic and diastolic blood pressures based on the mean blood pressure and the one of the systolic and diastolic blood pressures that has been determined.

The one or several IC(s) may determine both the mean blood pressure and the systolic blood pressure based on the dependence of the amplitudes of the blood volume pulses sensed at the finger abutment surface 24 on the pressure or force applied by the finger to the finger abutment surface 24 while the pressure or force increases as several successive blood volume pulses are recorded. The diastolic blood pressure may be computed by subtracting two times the difference between the systolic blood pressure and the mean blood pressure from the systolic blood pressure.

The one or several IC(s) may determine both the mean blood pressure and the diastolic blood pressure based on the dependence of the amplitudes of the blood volume pulses sensed at the finger abutment surface 24 on the pressure or force applied by the finger to the finger abutment surface 24 while the pressure or force decreases as several successive blood volume pulses are recorded. The systolic blood pressure may be computed by adding two times the difference between the mean blood pressure and the diastolic blood pressure to the diastolic blood pressure.

Figure 3:
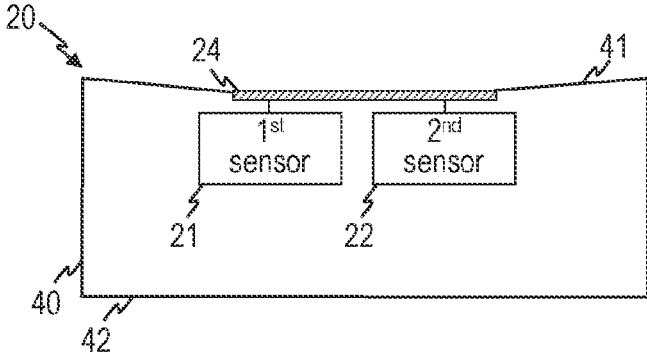
FIG. 3 is a schematic view of a sensor device.

FIG. 3 is a schematic view of the sensor device 20. The sensor device 20 has a housing 40. The housing has a first surface 41. The finger abutment surface 24 is provided on the first surface 41 of the housing 40.

The first surface 41 of the housing 40 may have a concavity or other recess. The finger abutment surface 24 may be provided within the concavity or recess. Such a configuration provides haptic feedback that aids correct positioning of the finger on the finger abutment surface 24.

A second surface 42 of the housing 40 may act as a counter-bearing surface that is rested against a support (which may be a user's hand or another support) as the finger is pressed against the finger abutment surface 24.

The sensor device 20 comprises a first sensor 21 operative to sense blood volume pulses. The first sensor 21 may be operative to sense blood volume pulses in the finger placed on the finger abutment surface 24. The first sensor 21 may comprise one or several of a bioimpedance sensor, a photoplethysmography (PPG) sensor, a piezoelectric sensor, an accelerometer, in particular a ballistographic sensor. The finger abutment surface 24 may operate as an electrode of the first sensor (e.g., when the first sensor 21 is implemented as a bioimpedance sensor).

The sensor device 20 comprises a second sensor 22. The second sensor 22 is operative to sense a pressure or force exerted onto the finger abutment surface 24.

The blood volume pulses and pressure or force may respectively be measured concurrently and in a time-resolved manner. The blood volume pulses and the pressure or force may be sensed as time-series data.

The sensor device 20 may comprise at least one IC operative to perform at least part of the data processing of amplitudes of the sensed blood pressure pulses and of the sensed pressure or force applied to the finger abutment surface 24.

The sensor device 20 may comprise control circuitry for controlling operation of at least the first sensor 21. The control circuitry may be operative to selectively activate the first sensor 21 in response to detecting that an activation criterion is fulfilled. The activation criterion may be dependent on an output of the second sensor 22. For illustration, the control circuitry may be operative to selectively activate the first sensor 21 for sensing blood pressure pulses in response to the pressure or force sensed by the second sensor 22 reaching an activation threshold. Power consumption of the sensor device 20 may be reduced thereby.

The sensor device 20 and system 10 operate without requiring activation of an electromechanical actuator, such as a pump. Pressure or force applied to blood vessels to intermittently pause blood flow for performing the blood pressure measurement is generated by the user pressing the finger against the finger abutment surface 24.

The first sensor 21 may comprise or may be a bioimpedance sensor. This allows blood volume pulses to be detected with a short response time. The bioimpedance sensor may sense the blood volume pulses without requiring optical components that may be prone to being damaged and/or compromised by dirt accumulation during use.

The finger abutment surface 24 may be a conductive surface. The finger abutment surface 24 may be one of the electrodes used by the bioimpedance sensor for measuring variations in bioimpedance, which are indicative of the pulsating blood flow in the user's finger.

The sensor device 20 may comprise a bioimpedance sensor surface that serves as second electrode for the bioimpedance measurement. The bioimpedance sensor surface may be a conductive surface arranged on the housing 40 of the sensor device.

FIG. 4, FIG. 5, and FIG. 6 illustrate various possible arrangements for the bioimpedance sensor surface 44.

FIG. 4 shows a sensor device 20 in which the bioimpedance sensor surface 44 is arranged at a side surface 43 of the housing 40 that extends transversely (e.g., at an angle of more than between 50° and 140°) from the first surface 41. The bioimpedance sensor surface 44 may be define a plane that is angled (i.e., arranged at an angle different form 0°) relative to the plane in which the finger abutment surface 24 extends.

FIG. 5 shows a sensor device 20 in which both the finger abutment surface 24 and the bioimpedance sensor surface 44 are arranged on the first surface 41. The finger abutment surface 24 and the bioimpedance sensor surface 44 may be offset from each other in a direction parallel to the first surface 41.

The finger abutment surface 24 may be arranged in a first recess on the first surface 41. The bioimpedance sensor surface 44 may be arranged in second recess on the first surface 41. The first and second recesses may be separated by a ridge extending therebetween. The first and second recesses provide haptic feedback that aids in positioning finger(s) for performing the bioimpedance measurement.

The bioimpedance sensor surface 44 may be dimensioned for receiving a fingertip thereon.

FIG. 6 shows a sensor device 20 in which the bioimpedance sensor surface 44 is arranged on a second surface 42 that is opposite the first surface 41 of the housing.

Arrangements as shown in FIGS. 4 and 6 facilitate bioimpedance sensing while the sensor device 20 is held in the hand. An arrangement as shown in FIG. 5 facilitates bioimpedance sensing while the sensor device 20 is rested on a support surface such as a table.

While FIGS. 4 to 6 illustrate implementations in which bioimpedance sensing may be performed between the finger abutment surface 24 and the bioimpedance sensor surface 44, plural distinct bioimpedance sensor electrodes may be provided that may, but do not need to overlap with the finger abutment surface 24.

FIG. 7 is a block diagram representation of a sensor device or system according to an embodiment. The sensor device or system comprises the first sensor 21 operative to sense blood volume pulses in the finger pressed against the finger abutment surface, the second sensor 22 operative to sense the force or pressure exerted onto the finger abutment surface, and processing circuitry 50. The processing circuitry may comprise one or several IC(s) in the sensor device 20 and/or, if present, one or several IC(s) in a computing device 30 communicatively coupled to the sensor device 20.

The processing circuitry 50 may be operative to determine a systolic blood pressure. The processing circuitry 50 may comprise or execute a systolic blood pressure determination module 51 operative to determine the systolic blood pressure based on amplitudes of the blood volume pulses and the pressure or force recorded at the time(s) at which the signal indicating the blood volume pulses has one or several local extrema (e.g., maxima). The systolic blood pressure determination module 51 may be operative to determine the systolic blood pressure from the amplitudes of the blood volume pulses and the pressure or force recorded while the pressure or force increases. Alternatively or additionally, the systolic blood pressure determination module 51 may be operative to determine the systolic blood pressure from a diastolic blood pressure and a mean blood pressure.

The processing circuitry 50 may be operative to determine a diastolic blood pressure. The processing circuitry 50 may comprise or execute a diastolic blood pressure determination module 52 operative to determine the diastolic blood pressure based on amplitudes of the blood volume pulses and the pressure or force recorded at the time(s) at which the signal indicating the blood volume pulses has one or several local extrema (e.g., maxima). The diastolic blood pressure determination module 52 may be operative to determine the systolic blood pressure from the amplitudes of the blood volume pulses and the pressure or force recorded while the pressure or force decreases. Alternatively or additionally, the diastolic blood pressure determination module 51 may be operative to determine the diastolic blood pressure from the systolic blood pressure and the mean blood pressure.

The processing circuitry 50 may comprise or be operative to execute a calibration routine module 53. The calibration routine module 53 may be operative to perform an absolute calibration for a blood pressure monitoring process that detects relative changes of the blood pressure. The calibration routine module 53 may be operative to determine an offset that must be added to a relative change in blood pressure to obtain the absolute value of the blood pressure. This may be done for the systolic and/or diastolic blood pressure. The calibration routine module 53 may be operative to perform a calibration of a pulse transit time (PTT)-based blood pressure monitoring technique.

Figures 8, 9:
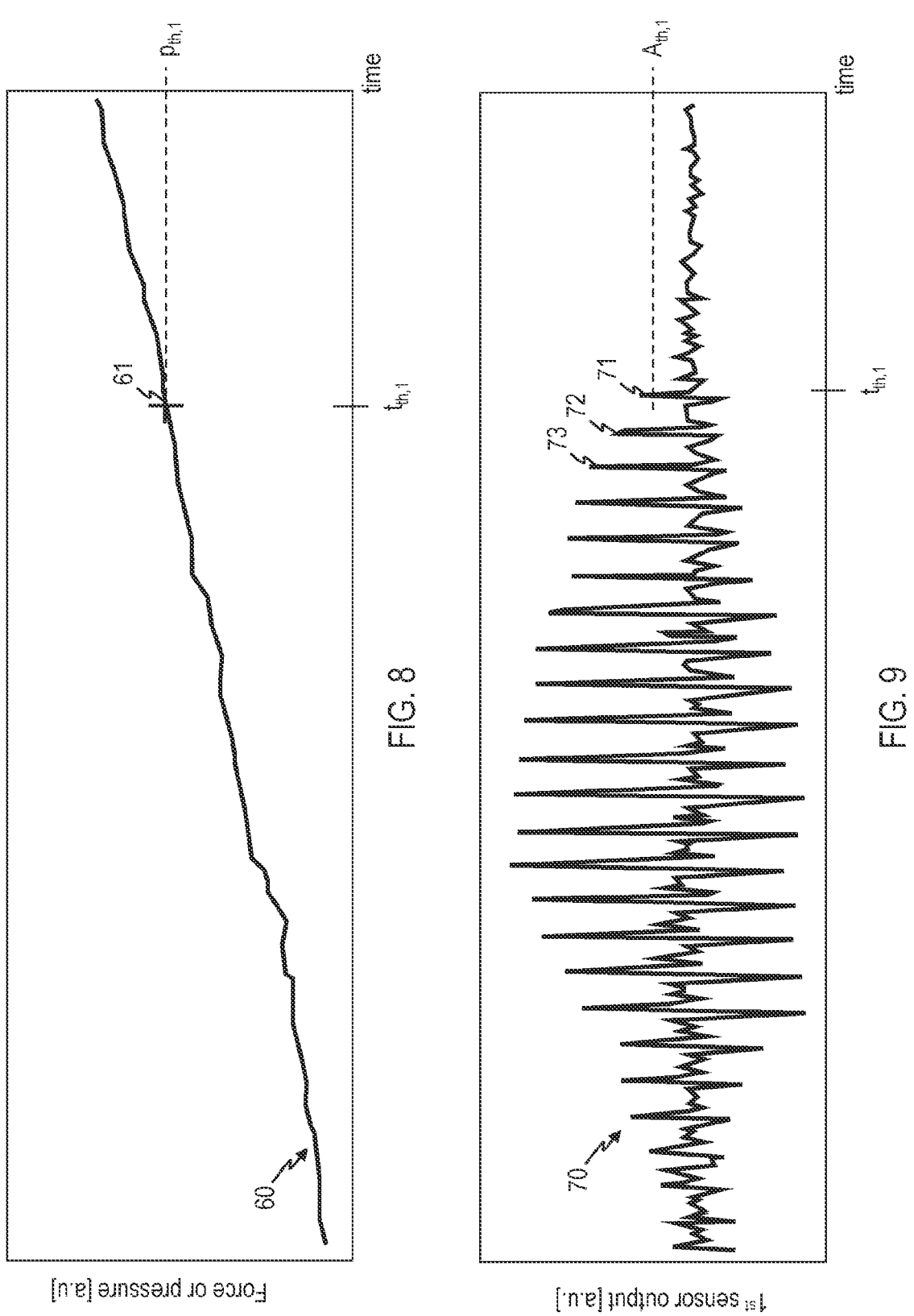
FIGS. 8 and 9 are graphs of exemplary sensor data processed by the sensor device and/or system.

FIG. 8 is a graph showing a pressure or force 60 as a function of time. In operation, the pressure or force 60 is sensed by the second sensor 22. The pressure or force 60 may be received by the processing circuitry 50 as time-series data for processing.

FIG. 9 is a graph showing blood volume pulses 70 as a function of time. In operation, the blood volume pulses 70 are sensed by the first sensor 21. The blood volume pulses 70 may be received by the processing circuitry 50 as time-series data for processing.

In order to determine a systolic blood pressure, instructions may be output to the user to increase the pressure or force with which the finger is pressed against the finger abutment surface 24.

In one exemplary implementation, determining the systolic blood pressure comprises the following steps performed by the processing circuitry 50 when an increase is observed in the pressure or force with which the finger is pressed against the finger abutment surface 24:

Identifying a last peak 71 in the blood volume pulses 70 that has a peak height that exceeds a first amplitude threshold $A_{th,1}$. The last peak 71 is defined by being a local maximum in the first sensor signal and there being no subsequently recorded peaks in the blood volume pulses 70 that exceed the first amplitude threshold $A_{th,1}$.

Determining a time td at which the last peak 71 is recorded.

Determining the pressure or force $p_{th,1}$ recorded at the time $t_{th,1}$.

The value of the second sensor signal output $p_{th,1}$ recorded at the time $t_{th,1}$ may be used as the systolic blood pressure (with an appropriate scaling factor that depends on the implementation of the second sensor).

More complex techniques may be employed. For illustration, interpolation or extrapolation techniques may be employed to more accurately determine the pressure or force at which the amplitude of the blood volume pulses reaches or falls below the first amplitude threshold when the pressure or force with which the finger is pressed against the finger abutment surface 24 increases. For illustration, the processing circuitry 50 may perform the following steps:

Identifying the last peak 71 in the blood volume pulses 70 that has a peak height that exceeds a first amplitude threshold $A_{th,1}$ and determining its peak height $A_{last}$.

Determining a time $t_{th,1}$ at which the last peak 71 is recorded.

Identifying at least one additional peak 72, 73 preceding the last peak 71 and determining the associated peak height(s) $A_{proc,j}$ (where j is an index designating the preceding peaks 72, 73)

Identifying the time(s) at which the at least one additional peak 72, 73 is/are recorded.

Determining the values of the second sensor output $p_{last}$ and $p_{proc,j}$ at the times at which the last peak 71 and the at least one preceding peak 72, 73 are recorded.

Performing a linear extrapolation or other linear regression analysis to determine the time at which the pressure or force reaches the first amplitude threshold $A_{th,1}$.

For illustration, if one additional peak 72 or 73 preceding the last peak 71 is used in the analysis, the pressure or force at which the first amplitude threshold $A_{th,1}$ is reached may be determined as:

$$p_{systolic} = p_{last} + \frac{p_{last} - p_{pfrec,j}}{A_{prec,j} - A_{last}} \times (A_{last} - A_{th,1}) \tag{1}$$

In Equation (1), $A_{proc,j}$ may be an amplitude of the peak 72 directly preceding the last peak 71 or of an even earlier peak 73 of the first sensor signal, and $p_{proc,j}$ denotes the second sensor output at the time at which the associated peak is recorded. As explained above, an appropriate scaling factor may be applied to the value of the second sensor signal $p_{systolic}$. The scaling factor depends on the implementation of the second sensor 22 and takes into account the relation between absolute force or pressure values and second sensor output.

Other techniques may be employed to determine the systolic blood pressure. For illustration, the processing circuitry 50 may process the first sensor output and the second sensor output to determine $N \geq 2$ pairs ($A_i$, $p_i$) of amplitude height $A_i$ in the blood volume pulses (first sensor output) and associated pressure or force $p_i$ (second sensor output) of curves recorded while the pressure or force increases, where i=1, . . . , N denotes an index. Linear or non-linear regression may be applied to the pairs ($A_i$, $p_i$) to determine the first sensor output at which the amplitude of the blood volume pulses reaches or falls below the first amplitude threshold $A_{th,1}$.

The first amplitude threshold $A_{th,1}$ may be dependent on the implementation of the first sensor. The first amplitude threshold $A_{th,1}$ may be set to be equal to or greater than a root-mean-square of noise in the first sensor output.

The first sensor output and the second sensor output determined from the data recorded while the force or pressure applied by the finger against the finger abutment surface 24 (indicated by the increasing ramp in the second sensor output 60) increases may not only be used to determine the systolic blood pressure, but may also be used to determine a mean blood pressure (the average of systolic and diastolic blood pressures). For illustration, the functional dependence of the amplitudes of the blood volume pulses on the pressure or force may be processed to determine both the systolic blood pressure and the mean blood pressure (based on, e.g., the value of the second sensor output 60 at the time at which the amplitudes of the blood volume pulses in the first sensor output 70 start decreasing). The diastolic blood pressure may then be determined based on the systolic blood pressure and the mean blood pressure as $$p_{diastol} = p_{systolic} - 2 \times (p_{systolic} - p_{mean}) \tag{2}.$$

Alternatively or additionally, in order to determine a diastolic blood pressure, instructions may be output to the user to decrease the pressure or force with which the finger is pressed against the finger abutment surface 24.

In one exemplary implementation, determining the diastolic blood pressure comprises the following steps performed by the processing circuitry 50 when a decrease is observed in the pressure or force with which the finger is pressed against the finger abutment surface 24:

Identifying a last peak in the blood volume pulses of the first sensor output that has a peak height that exceeds a second amplitude threshold $A_{th,2}$. The last peak is defined by being a local maximum in the first sensor signal and there being no subsequently recorded peaks in the blood volume pulses of the first sensor output that exceed the second amplitude threshold $A_{th,2}$.

Determining a time $t_{th,2}$ at which the last peak is recorded.

Determining the pressure or force $p_{th,2}$ recorded at the time $t_{th,2}$.

The value of the second sensor signal output $p_{th,2}$ recorded at the time $t_{th,2}$ may be used as the systolic blood pressure (with an appropriate scaling factor being applied that defines the relation between the second sensor output and pressure).

More refined techniques may be employed. For illustration, interpolation or extrapolation techniques may be employed to more accurately determine the pressure or force at which the amplitude of the blood volume pulses reaches or falls below the second amplitude threshold when the pressure or force with which the finger is pressed against the finger abutment surface 24 decreases, in order to determine the diastolic blood pressure. For illustration, the processing circuitry 50 may perform the steps explained with reference to determination of the systolic blood pressure above, in order to determine the systolic blood pressure from the first and second sensor outputs while the pressure or force with which the finger is pressed against the finger abutment surface 24 decreases.

Other techniques may be employed to determine the diastolic blood pressure. For illustration, the processing circuitry 50 may process the first sensor output and the second sensor output to determine N≥2 pairs $(A_i, p_i)$ of amplitude height $A_i$ in the blood volume pulses (first sensor output) and associated pressure or force $p_i$ (second sensor output) of curves recorded while the pressure or force decreases, where i=1, ..., N denotes an index. Linear or non-linear regression may be applied to the pairs $(A_i, p_i)$ to determine the first sensor output at which the amplitude of the blood volume pulses reaches or falls below the second amplitude threshold $A_{th,2}$.

The second amplitude threshold $A_{th,2}$ may be dependent on the implementation of the first sensor. The second amplitude threshold $A_{th,2}$ may be set to be equal to or greater than a root-mean-square of noise in the first sensor output. The second amplitude threshold $A_{th,2}$ may be equal to or different from the first amplitude threshold $A_{th,1}$.

The first sensor output and the second sensor output determined from the data recorded while the force or pressure applied by the finger against the finger abutment surface 24 (indicated by the increasing ramp in the second sensor output) decreases may not only be used to determine the systolic blood pressure, but may also be used to determine a mean blood pressure (the average of systolic and diastolic blood pressures). For illustration, the functional dependence of the amplitudes of the blood volume pulses on the pressure or force may be processed to determine both the diastolic blood pressure and the mean blood pressure (based on, e.g., the value of the second sensor output at the time at which the amplitudes of the blood volume pulses in the first sensor output start decreasing). The systolic blood pressure may then be determined based on the diastolic blood pressure and the mean blood pressure as $$p_{systolic} = p_{diastol} + 2 \times (p_{mean} - p_{diastol}) \tag{3}.$$

While techniques of determining the systolic, diastolic and/or mean blood pressure have been explained with reference to a scenario in which the pressure or force exerted on the finger abutment surface increases (i.e., there is a rising force or pressure ramp), the systolic, diastolic and/or mean blood pressure may be determined from the first sensor output and the second sensor output recorded while the pressure or force exerted on the finger abutment surface decreases.

For illustration, a user may initially press the finger against the finger abutment surface 24 with a pressure or force which is so strong that no significant blood volume pulses are recorded. As the pressure or force is decreased, the change in amplitude of the blood volume pulses is recorded.

Figures 15, 16:
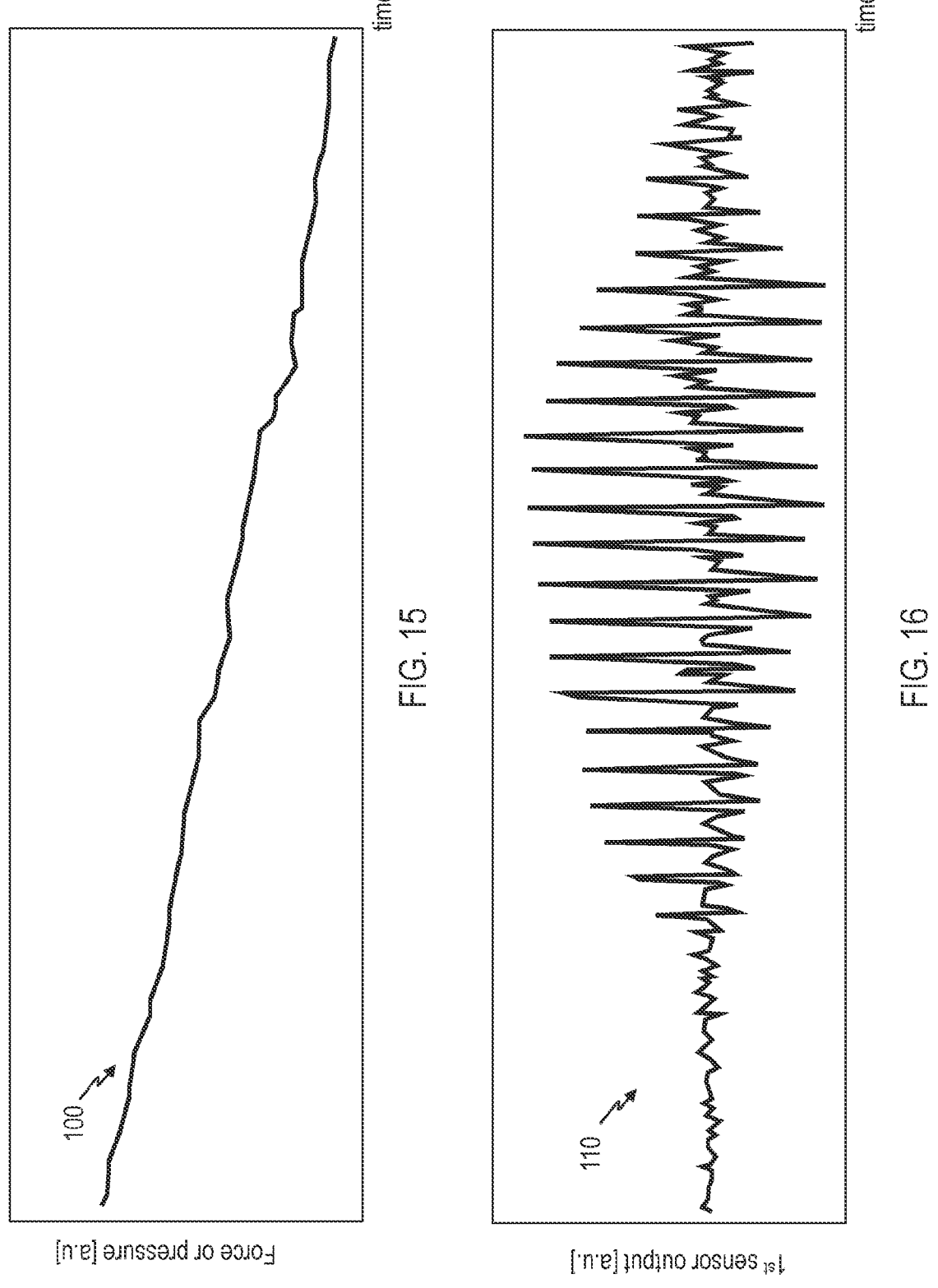
FIGS. 15 and 16 are graphs of exemplary sensor data processed by the sensor device and/or system.

FIG. 15 shows an exemplary second sensor output 100 for a case in which the pressure or force is decreased. FIG. 16 shows an exemplary first sensor output 110. The variation in amplitude and associated pressure or force allows the systolic, diastolic and/or mean blood pressure to be determined. For illustration, one or several threshold comparisons may be employed to identify peaks in the first sensor output 110. The pressure or force at the times at which the blood volume pulses reach certain threshold may be determined from the second sensor output 100 and may be used to determine the systolic, diastolic and/or mean blood pressure.

The absolute blood pressure values may be determined from first and second sensor output recorded while the force or pressure varies in a non-monotonous manner. For illustration, a user may first increase the force or pressure exerted by the finger against the finger abutment surface 24 and may subsequently decrease the force or pressure, or vice versa. This may be done, under instructions issued via the user interface, in a playful manner until sufficient data has been acquired. As the pressure or force increases and decreases once or several times, the change in amplitude of the blood volume pulses is recorded and processed.

Figures 17, 18:
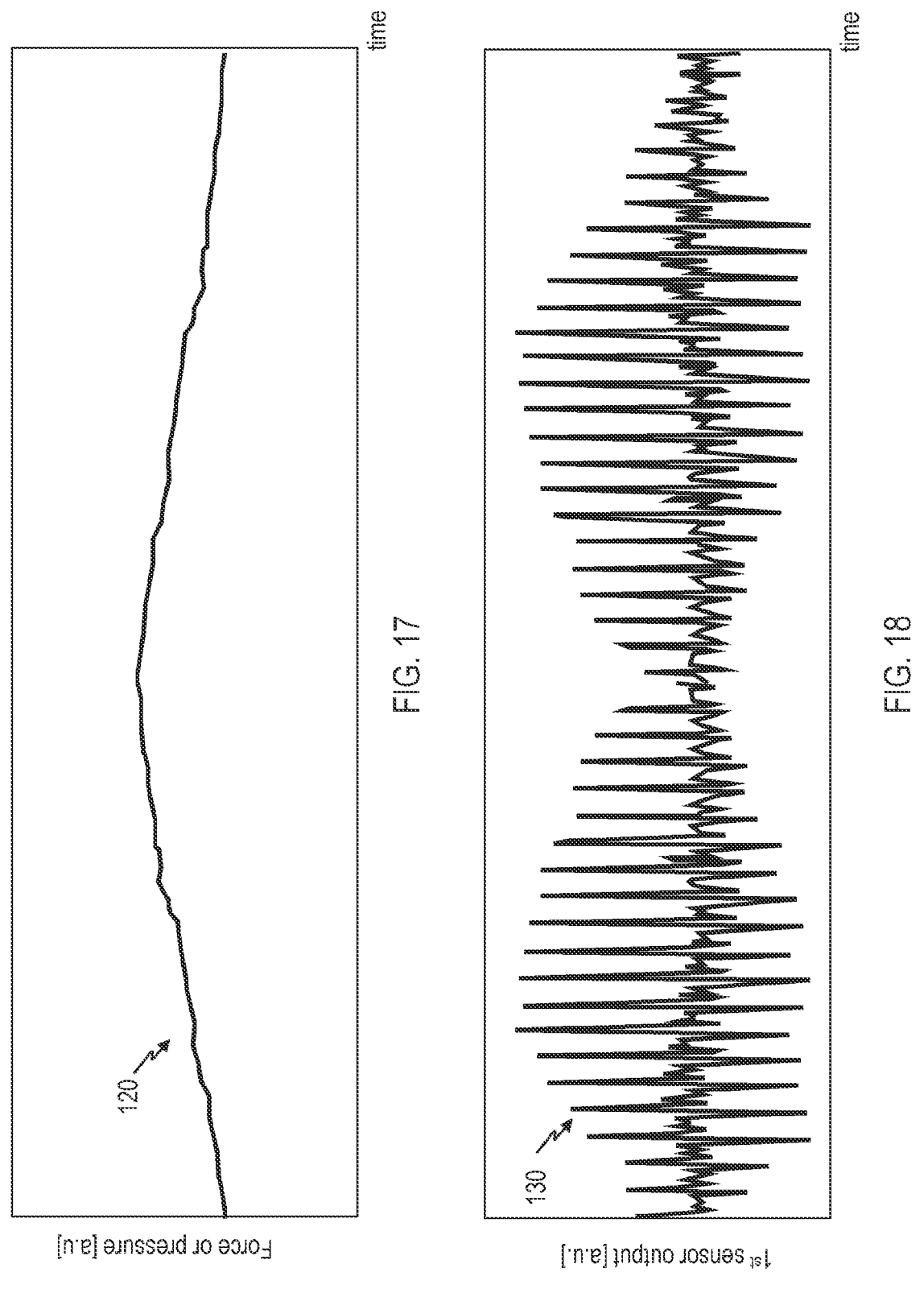
FIGS. 17 and 18 are graphs of exemplary sensor data processed by the sensor device and/or system.

FIG. 17 shows an exemplary second sensor output 120 for a case in which the pressure or force varies non-monotonously. FIG. 18 shows an exemplary first sensor output 130. The variation in amplitude and associated pressure or force allows the systolic, diastolic and/or mean blood pressure to be determined. For illustration, one or several threshold comparisons may be employed to identify peaks in the first sensor output 130. The pressure or force at the times at which the blood volume pulses reach certain threshold may be determined from the second sensor output 120 and may be used to determine the systolic, diastolic and/or mean blood pressure.

Figure 10:
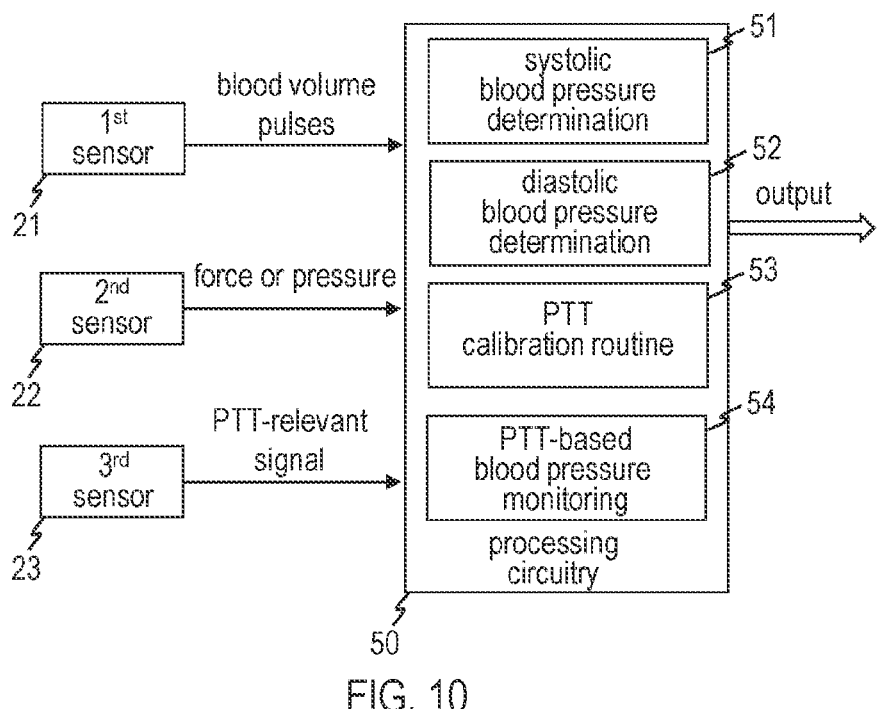
FIG. 10 is a functional block diagram representation of components of the sensor device and/or system.

FIG. 10 is a block diagram of a sensor device or system according to an embodiment which is capable of performing a pulse transit time (PTT)-based blood pressure monitoring. PTT-based techniques can provide only rough estimates of absolute values of the blood pressure, but provide more reliable information on changes in blood pressure.

In the sensor device or system of FIG. 10, the processing of the first sensor output and second sensor output is combined with a PTT-based blood pressure monitoring. To perform the PTT-based blood pressure monitoring, the processing circuitry 50 may receive at least one PTT-relevant signal for determining the PIT from a third sensor 23. The third sensor 23 may be an ECG sensor.

The processing circuitry 50 is operative to execute a FIT-based blood pressure monitoring module 54. The PIT-based blood pressure monitoring module 54 is operative to determine a FIT of blood volume pulses based on the PTT-relevant signal received from the third sensor 23 and a signal indicating the blood volume pulses (which may, but does not need to be sensed by the first sensor 21). The PTT-based blood pressure monitoring module 54 may be operative to determine changes in blood pressure from changes in PTT. The PTT may be determined as time difference between a peak in the ECG signal and of the blood volume pulse.

The changes in blood pressure determined by PTT-based blood pressure monitoring may be combined with the absolute value(s) of the systolic and/or diastolic blood pressure determined by processing the first sensor output and the second sensor output. For illustration, the absolute value(s) of the systolic and/or diastolic blood pressure may be initially determined and used to calibrate the PTT-based blood pressure monitoring. In this manner, an offset is defined that allows absolute values of systolic and/or diastolic blood pressure to be determined from absolute value(s) of the systolic and/or diastolic blood pressure(s) determined by processing the first sensor output indicative of blood volume pulses and the second sensor output indicative of the force or pressure exerted on the finger abutment surface 24, the PTT recorded concurrently with determining the absolute value(s) of the systolic and/or diastolic blood pressure(s), and the subsequent change in PTT.

The first one of these quantities defines the initial value of the systolic and/or diastolic blood pressure(s), and the second and third ones of these quantities provide a subsequent change that is added to or subtracted from the initial value of the systolic and/or diastolic blood pressure(s). In this manner, the absolute value(s) of the systolic and/or diastolic blood pressure(s) can be determined even when the user discontinues pressing his/her finger against the finger abutment surface. The calibration of the PIT-based blood pressure monitoring may be performed by a PTT calibration routine module 53.

Alternatively or additionally to using the first sensor output indicating the blood volume pulses and the second sensor output indicating the pressure or force exerted on the finger abutment surface for implementing the FIT calibration, the PTT-based blood pressure monitoring may be used to estimate the systolic and/or diastolic blood pressure(s). Instructions to the user may be generated for outputting via the UT 25, 35 that direct the user to change the pressure or force applied by the finger against the finger abutment surface 24, based on the blood pressure estimates obtained from the PTT-based blood pressure monitoring. For illustration, instructions may be generated that instruct the user to increase the pressure or force so as to more rapidly reach a pressure close to the systolic blood pressure. Alternatively or additionally, instructions may be generated that instruct the user to change the pressure or force so as to more rapidly reach a pressure close to the diastolic blood pressure.

Figure 11:
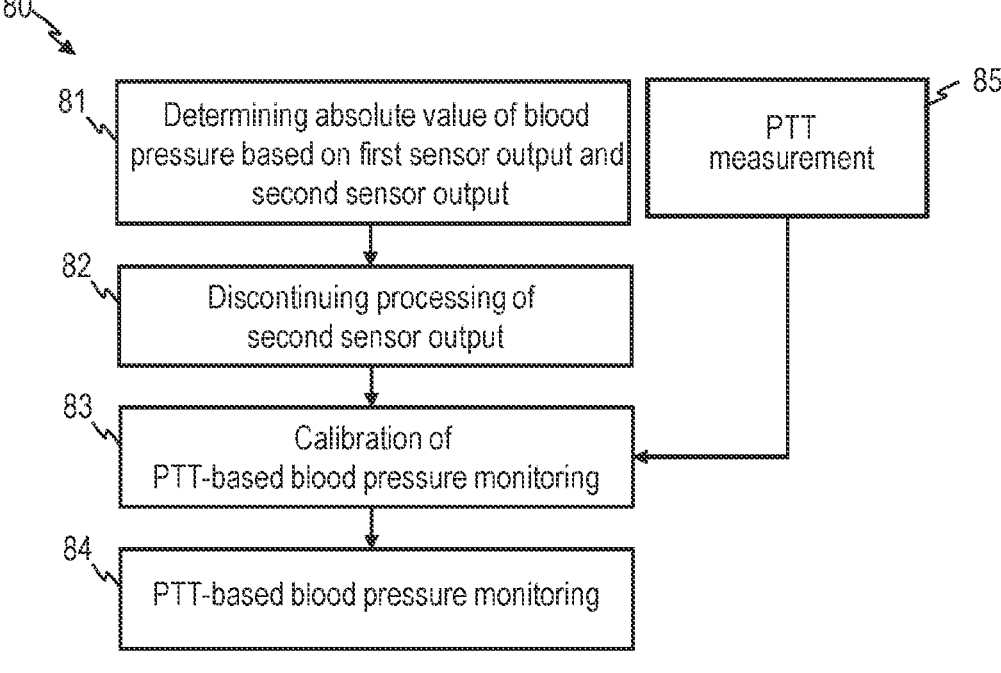
FIG. 11 is a flow chart of a method.

FIG. 11 is a flow chart of a method 80. The method 80 may be performed automatically by or using the sensor device or system according to the invention.

At step 81, absolute value(s) of the systolic and/or diastolic blood pressure(s) are determined from sensed blood volume pulses in the first sensor output and the pressure or force indicated by the second sensor output. A PTT measurement is performed concurrently at step 85.

At step 82, the monitoring and processing of the force or pressure applied to the finger abutment surface is discontinued.

At step 83, the absolute value(s) of the systolic and/or diastolic blood pressure(s) are used in combination with the FIT measurement of step 85 to perform a calibration of the FIT-based blood pressure technique. This amounts to determining offset(s) that must be added to the change in blood pressure derived from PTT measurements to arrive at the systolic and/or diastolic blood pressure(s).

At step 84, FIT-based blood pressure monitoring is performed. Changes in blood pressure may be determined based on the difference between the PTT determined at step 84 and the FIT determined at step 85. The change in blood pressure determined from the change in PTT is added to the absolute value(s) of the systolic and/or diastolic blood pressure(s) determined at step 83 to obtain absolute value(s) of the systolic and/or diastolic blood pressure(s) on an ongoing basis, even when the user does no longer press his/her finger against the finger abutment surface 24.

Figure 12:
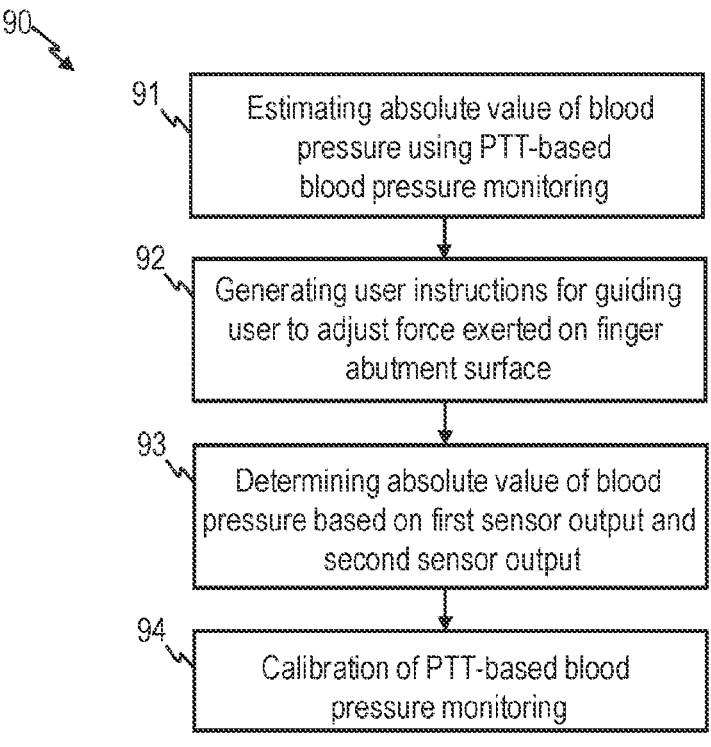
FIG. 12 is a flow chart of a method.

FIG. 12 is a flow chart of a method 90. The method 90 may be performed automatically by or using the sensor device or system according to the invention.

At step 91, absolute value(s) of the systolic and/or diastolic blood pressure(s) are estimated using a PTT-based technique. Subsequently, the estimates for the absolute value(s) of the systolic and/or diastolic blood pressure(s) are used to efficiently determine the systolic and/or diastolic blood pressure(s) more accurately.

In one implementation, this may be achieved by guiding the user to facilitate the determination of the systolic and/or diastolic blood pressure(s) from the blood volume pulses (first sensor signal) and the pressure or force (second sensor signal).

At step 92, user instructions may be generated for guiding the user to adjust the force exerted onto the finger abutment surface 24. The user instructions are generated based on the estimate obtained from the PTT-based technique at step 91. The user instructions may cause the user to change the force or pressure exerted onto the finger abutment surface 24 so as to more rapidly approach the relevant pressure ranges close to the systolic or diastolic blood pressures.

At step 93, the absolute value(s) of the systolic and/or diastolic blood pressure(s) may be determined based on the first and second sensor outputs, as described in detail herein.

At step 94, the FIT-based blood pressure monitoring may optionally be calibrated using the absolute value(s) of the systolic and/or diastolic blood pressure(s) determined at step 93. This may be done in the same manner as described with reference to FIG. 11.

Figure 13:
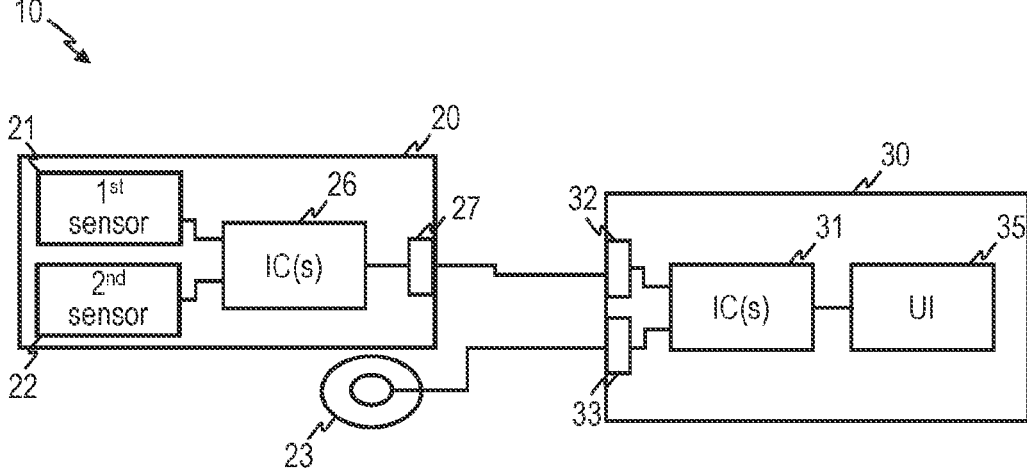
FIG. 13 is a block diagram of a system comprising a sensor device.

FIG. 13 is a block diagram of a system 10 according to an embodiment. The system 10 comprises the sensor device 20 communicatively coupled to the computing device 30. Outputs of the first sensor 21 and of the second sensor 22 may be processed, at least in part, by one or several IC(s) 26 of the sensor device 20. The one or several IC(s) 26 are integrated within the housing of the sensor device 20. The one or several IC(s) 26 may perform various functions, such as signal conditioning, identifying peaks of the blood volume pulses in the first sensor output, determining peak heights, and/or determining the pressure or force reflected by the second sensor output at the time at which the peak(s) is/are detected. The one or several IC(s) 26 may be operative to determine the systolic and/or diastolic blood pressure(s).

The sensor device 20 has an interface 27 operative for communicative wired or wireless coupling to an interface 32 of the computing device 30. The sensor device 20 is operative to output information obtained by (pre-)processing the first sensor output and the second sensor output to the computing device 30.

The computing device 30 comprises one or several IC(s) 31. The one or several IC(s) 31 of the computing device 30 may perform additional processing steps on the data received at the interface 32 from the sensor device 20.

For illustration, the computing device 30 may have a wired or wireless interface 33 for communicative coupling with the third sensor 23 (which may be an ECG sensor). The one or several IC(s) 31 may be operative to determine the systolic and/or diastolic blood pressure(s) (if this has not yet been done by the IC(s) 26) and/or to perform a calibration of a PTT-based blood pressure monitoring.

Figure 14:
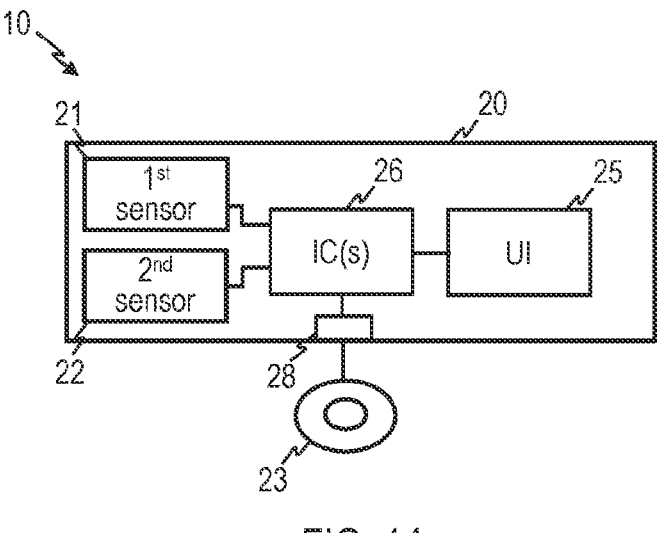
FIG. 14 is a block diagram of a sensor device.

FIG. 14 is a block diagram of the sensor device 20. The sensor device 20 comprises the first and second sensors 21, 22 integrated within a housing of the sensor device 20.

The sensor device 20 may have a wired or wireless interface 28 for communicative coupling with the third sensor 23 (which may be an ECG sensor).

The sensor device 20 comprises one or several IC(s) 26 of the sensor device 20. The one or several IC(s) 26 are integrated within the housing of the sensor device 20. The one or several IC(s) 26 may perform various functions, such as signal conditioning, identifying peaks of the blood volume pulses in the first sensor output, determining peak heights, and/or determining the pressure or force reflected by the second sensor output at the time at which the peak(s) is/are detected. The one or several IC(s) 26 may be operative to determine the systolic and/or diastolic blood pressure(s).

The one or several IC(s) 26 may be operative to perform a PTT-based blood pressure monitoring. The PTT-based blood pressure monitoring may comprise processing ECG signals received from the third sensor 23 in combination with the blood volume pulses to determine changes in PTT.

The one or several IC(s) 26 may be operative to perform a calibration of the PTT-based blood pressure monitoring using the systolic and/or diastolic blood pressure(s) determined from the outputs of the first and second sensors 21, 22, as more thoroughly described above.

The one or several IC(s) 26 may be operative to generate information for outputting via a UI 25 integrated within the sensor device 20 and/or via a UI 35 separate from the sensor device 20 and/or for storing in a data storage device (e.g., for long-time monitoring and/or analysis). The information for outputting may comprise the determine systolic and/or diastolic blood pressure(s) or information derived therefrom, instructions for the user for changing the force or pressure exerted against the finger abutment surface 24, or other information.

While exemplary embodiments have been described with reference to the Figures, modifications may be implemented in other embodiments. While the devices, systems and methods can provide biofeedback, the determined systolic and/or diastolic blood pressures may alternatively or additionally be transmitted to a data storage device for storage and further use. For further illustration, the techniques of the application may include PTT-based blood pressure monitoring, it is not required that the determined systolic and/or diastolic blood pressures be used for calibrating PTT-based blood pressure monitoring or otherwise be combined with PTT-based blood pressure monitoring.

Although the present invention has been described with reference to preferred embodiments, workers skilled in the art will recognize that changes may be made in form and detail without departing from the spirit and scope of the invention.

The invention claimed is:

1. A sensor system for performing a blood pressure measurement, comprising:
   a finger abutment surface;
   a first sensor operative to sense blood volume pulses in a finger pressed on the finger abutment surface;
   a second sensor operative to sense a force or pressure with which the finger is pressed on the finger abutment surface;
   an electrocardiogram (ECG) sensor operative to sense ECG signals while the first sensor concurrently senses the blood volume pulses; and
   processing circuitry operative to:
      process amplitudes of the sensed blood volume pulses and the sensed force or pressure with which the finger is pressed on the finger abutment surface to determine an absolute blood pressure,
      process an output of an ECG sensor and of the first sensor to determine pulse transit times (PTTs) of the blood volume pulses and to process the PTTs to determine a change in blood pressure, and
      generate user instructions for adjusting the force or pressure based on the determined PTTs;
      wherein the sensor system is configured to estimate at least one of a systolic blood pressure and a diastolic blood pressure and generate the user instructions that direct the user to change the pressure or force applied by the finger against the finger abutment surface based on the blood pressure estimate(s) obtained from the PTT-based blood pressure monitoring.

2. The sensor system of claim 1, wherein the first sensor comprises a bioimpedance sensor.

3. The sensor system of claim 2, wherein the bioimpedance sensor comprises an electrode on the finger abutment surface to be contacted by the finger pressed on the finger abutment surface and another electrode arranged transversely to and/or offset from the finger abutment surface to be contacted by another finger or by a hand holding the system.

4. The sensor system of claim 1, wherein the processing circuitry is operative to execute a calibration routine for calibrating a PTT-based blood pressure monitoring process, the calibration routine using, as an input, the absolute blood pressure determined based on the amplitudes of the sensed blood volume pulses and the sensed force or pressure.

5. The sensor system of claim 1, wherein the first sensor comprises at least one of: a photoplethysmography (PPG) sensor, a piezoelectric sensor, and/or a ballistographic sensor.

6. The sensor system of claim 1, wherein the processing circuitry is operative to process the amplitudes of the sensed blood volume pulses and the sensed force or pressure to determine one or several of
   a systolic blood pressure,
   a diastolic blood pressure, and/or
   a mean blood pressure that is a mean value of the systolic and diastolic blood pressures.

7. The sensor system of claim 6, wherein the processing circuitry is operative to:

determine the systolic and/or diastolic blood pressure based on the force or pressure ($p_{th,1}$) sensed by the second sensor in at least one pulse that is identified based on a threshold comparison of the amplitude of the blood volume pulses sensed by the first sensor, and/or determine the diastolic blood pressure based on (i) a change in the amplitudes of the sensed blood volume pulses as a function of the sensed force or pressure or (ii) the systolic blood pressure and the mean blood pressure, and/or determine the systolic blood pressure based on (i) a change in the amplitudes of the sensed blood volume pulses as a function of the sensed force or pressure or (ii) the diastolic blood pressure and the mean blood pressure.

8. The sensor system of claim 6, wherein the processing circuitry is operative to:

determine N≥2 pairs of values each consisting of an amplitude height in the blood volume pulses and an associated pressure or force recorded while the pressure or force increases, and apply a linear or non-linear regression to the pairs of values to determine a first sensor output at which the amplitude of the blood volume pulses reaches a first amplitude threshold ($A_{th,1}$) to determine the systolic blood pressure.

9. The sensor system of claim 6, wherein the processing circuitry is operative to:

determine N≥2 pairs of values each consisting of an amplitude height in the blood volume pulses and an associated pressure or force recorded while the pressure or force decreases, and apply a linear or non-linear regression to the pairs of values to determine a first sensor output at which the amplitude of the blood volume pulses reaches or falls below a second amplitude threshold ($A_{th,2}$), to determine the diastolic blood pressure.

10. The sensor system of claim 1, further comprising a user interface operative to output:

user instructions to cause the user to change the force or pressure, and/or information indicating the determined blood pressure.

11. The sensor system of claim 1, wherein the sensor system is a cuffless system.

12. The sensor system of claim 1, wherein the sensor system is operative to determine the absolute blood pressure without activation of an electromechanical actuator.

13. The sensor system of claim 1, further comprising:

a communication interface for communicatively coupling the first and second sensors to at least part of the processing circuitry, and a housing comprising the finger abutment surface, wherein the first sensor, the second sensor, and the communication interface are arranged in or on the housing.

14. The sensor system of claim 13, wherein the housing comprises a depression in which the finger abutment surface is arranged.

15. A method of performing a blood pressure measurement, comprising:

receiving a first sensor output representing sensed blood volume pulses in a finger pressed on a finger abutment surface;

receiving a second sensor output representing a sensed force or pressure with which the finger is pressed on the finger abutment surface;

receiving ECG signals sensed while the first sensor concurrently senses the blood volume pulses;

processing, by processing circuitry, amplitudes of the sensed blood volume pulses and the sensed force or pressure to determine an absolute blood pressure;

processing, by the processing circuitry, the ECG signals and the first sensor output to determine pulse transit times, PTTs, of the blood volume pulses;

processing, by the processing circuitry, the PTTs to determine a change in blood pressure; and estimating at least one of a systolic blood pressure and a diastolic blood pressure;

generating, by the processing circuitry, user instructions that direct the user to change the pressure or force applied by the finger against the finger abutment surface based on the blood pressure estimate(s) obtained from the PTT-based blood pressure monitoring.

16. The method of claim 15, wherein the method is performed by the sensor system of claim 1.

17. The sensor system of claim 6, wherein the processing circuitry is operative to:

determine the diastolic blood pressure based on (i) a change in the amplitudes of the sensed blood volume pulses as a function of the sensed force or pressure or (ii) the systolic blood pressure and the mean blood pressure, and determine the systolic blood pressure based on (i) a change in the amplitudes of the sensed blood volume pulses as a function of the sensed force or pressure or (ii) the diastolic blood pressure and the mean blood pressure.

* * * * *